(12) United States Patent
Ahmed et al.

(10) Patent No.: US 7,493,153 B2
(45) Date of Patent: Feb. 17, 2009

(54) AUGMENTED REALITY SYSTEM CONTROLLED BY PROBE POSITION

(75) Inventors: Syed Nadeem Ahmed, Bukit Batok (SG); Ralf Alfons Kockro, Eucalia Block (SG)

(73) Assignee: Volume Interactions Pte., Ltd., Singapore (SG)

( * ) Notice: Subject to any disclaimer, the term of this patent is extended or adjusted under 35 U.S.C. 154(b) by 132 days.

(21) Appl. No.: 10/480,490

(22) PCT Filed: Jun. 13, 2001

(86) PCT No.: PCT/SG01/00118

§ 371 (c)(1),
(2), (4) Date: Aug. 25, 2004

(87) PCT Pub. No.: WO02/100284

PCT Pub. Date: Dec. 19, 2002

(65) Prior Publication Data

US 2005/0203367 A1    Sep. 15, 2005

(51) Int. Cl.
*A61B 5/00* (2006.01)
(52) U.S. Cl. .................. 600/407; 600/424; 600/427; 600/429; 606/130; 345/7
(58) Field of Classification Search .......... 600/411, 600/417, 427, 429, 424, 407; 606/130; 382/128; 345/7
See application file for complete search history.

(56) References Cited

U.S. PATENT DOCUMENTS

| | | | | |
|---|---|---|---|---|
| 6,711,429 B1 * | 3/2004 | Gilboa et al. | .............. | 600/407 |
| 2004/0254454 A1 * | 12/2004 | Kockro | .............. | 600/424 |
| 2005/0015005 A1 * | 1/2005 | Kockro | .............. | 600/427 |
| 2005/0069188 A1 * | 3/2005 | Rubbert et al. | .............. | 382/128 |
| 2005/0206583 A1 * | 9/2005 | Lemelson et al. | .............. | 345/7 |
| 2006/0020204 A1 * | 1/2006 | Serra et al. | .............. | 600/437 |

OTHER PUBLICATIONS

Peters. Image-guided surgery: From X-rays to Virtual Reality. Comput Methods Biomech Biomed Engin. 2000;4(1):27-57.*
Gabbard. A Taxonomy of Usability Characteristics in Virtual Environments. Master Thesis: Virginia Polytechnic Institute and State University, 1997.*

* cited by examiner

*Primary Examiner*—Ruth S Smith
*Assistant Examiner*—Parikha S Mehta
(74) *Attorney, Agent, or Firm*—Aaron S. Haleva; Kramer Levin Naftalis & Frankel LLP (57) ABSTRACT

A guide system for use by a user who performs an operation in a defined three-dimensional region is disclosed, the system including a data processing apparatus for generating images of the subject of the operation in co-registration with the subject, a display for displaying the images to the user, a probe having a position which is visible to the user, and a tracking unit for tracking the location of the probe by the system and transmitting that location to the data processing apparatus, the data processing apparatus being arranged, upon the user moving the probe to a selection region outside and surrounding the defined region, to generate one or more virtual buttons, each of the buttons being associated with a corresponding instruction to the system, the data processing apparatus being arranged to register a selection by the user of any of the virtual buttons, the selection including positioning of the probe in relation to the apparent position of that virtual button, and to modify the computer-generated image based on the selection.

17 Claims, 8 Drawing Sheets

Fig. 6a - Virtual image generated by the computer

Fig. 6b - Real image

Fig. 6c - Virtual and real images overlaid together

AUGMENTED REALITY SYSTEM CONTROLLED BY PROBE POSITION

This application is the national stage filing of corresponding international application number PCT/SG01/00118, filed Jun. 13, 2001.

FIELD OF THE INVENTION

The present invention relates to a guide system, more particularly but not exclusively to a surgical navigation system for aiding a surgeon in performing an operation. The invention further relates to a method and device for controlling such a system.

BACKGROUND OF THE INVENTION

Image guidance systems have been widely adopted in neurosurgery and have been proven to increase the accuracy and reduce the invasiveness of a wide range of surgical procedures. Currently, image guided surgical systems ("Navigation Systems") are based on a series of images constructed from data gathered before the operation (for example by MRI or CT) which are registered in relation to the patient in the physical world by means of an optical tracking system. To do this, detecting markers are placed on the skin of the patient and they are correlated with their counterparts visible on the imaging data. During the surgical operation the images are displayed on a screen in 3 orthogonal planes through the image volume, while the surgeon holds a probe that is tracked by the tracking system. When the probe is introduced into the surgical field, the position of the probe tip is represented as an icon drawn on the images. By linking the preoperative imaging data with the actual surgical space, navigation systems provide the surgeon with valuable information about the exact localisation of a tool in relation to the surrounding structures and help to relate the intra-operative status to the pre-operative planning.

Despite these strengths, the current navigation systems suffer from various shortcomings.

Firstly, the surgeon needs to look at the computer monitor and away from the surgical scene during the navigation procedure. This tends to interrupt the surgical workflow and in practice often results in the operation being a two-people job, with the surgeon looking at the surgical scene through the microscope and his assistant looking at the monitor and prompting him.

Secondly, the interaction with the images during the surgery (e.g. switching between CT and MRI, changing the screen windows, activating markers or segmented structures from the planning phase, colour and contrast adjustments) requires the operation of a keyboard, a mouse or a touch screen, which is distracting for the surgeon and troublesome since the equipment needs to be packed with sterile drape. Although probe-type control devices have been proposed (see Hinckley K, Pausch R, Goble C J, Kassel N, F: A Survey of Design Issues in Spatial Input, Proceedings of ACM UIST'94 Symposium on User Interface Software & Technology, pp. 213-222; and Mackinlay J, Card S. Robertson G: Rapid Controlled Movement Through a Virtual 3D Workspace, Comp. Grap., 24 (4), 1990, 171-176), all have shortcomings in use.

Thirdly, a common problem to all current navigation systems which present imaging data as 2D orthogonal slices is the fact that the surgeon has to relate the spatial orientation of the image series including their mentally reconstructed 3D information to the orientation of the patient's head, which is covered during the operation.

A system that uses see-through augmentation by combining the naked eye view of the patient with the computer-generated images is currently under investigation (see Blackwell M, O'Toole R V, Morgan F, Gregor L: Performance and Accuracy experiments with 3D and 2D Image overlay systems. Proceedings of MRCAS 95, Baltimore, USA, 1995, pp 312-317; and DiGioia, Anthony M., Branislav Jaramaz, Robert V. O'Toole, David A. Simon, and Takeo Kanade. Medical Robotics And Computer Assisted Surgery In Orthopaedics. In Interactive Technology and the New Paradigm for Healthcare, ed. K. Morgan, R. M. Satava, H. B. Sieberg, R. Mattheus, and J. P. Christensen. 88-90. IOS Press, 1995). In this system, an inverted image on an upside-down monitor is overlaid over the surgical scene with a half-silvered mirror to combine the images. The user wears a head tracking system while looking onto the mirror and the patient beneath. However, the authors report significant inaccuracies between the virtual and the real object.

Other systems currently under research or development combine computer-generated images with the video of the surgical scene obtained through cameras placed at fixed positions in the operation theatre or a head mounted display of the user. The combined signal is then channelled into the HMD ("Head Mounted Display") of a user. The three examples of such projects are disclosed at in Fuchs H, Mark A, Livingston, Ramesh Raskar, D'nardo Colucci, Kurtis Keller, Andrei State, Jessica R. Crawford, Paul Rademacher, Samuel H. Drake, and Anthony A. Meyer, MD. Augmented Reality Visualization for Laparoscopic Surgery. Proceedings of First International Conference on Medical Image Computing and Computer-Assisted Intervention (MICCAI '98), 11-13 Oct. 1998, Massachusetts Institute of Technology, Cambridge, Mass., USA; Fuchs H, State A, Pisano E D, Garrett W F, Gentaro Hirota, Mark A. Livingston, Mary C. Whitton, Pizer S M. (Towards) Performing Ultrasound-Guided Needle Biopsies from within a Head-Mounted Display. Proceedings of Visualization in Biomedical Computing 1996, (Hamburg, Germany, Sep. 22-25, 1996), pgs. 591-600; and State, Andrei, Mark A. Livingston, Gentaro Hirota, William F. Garrett, Mary C. Whitton, Henry Fuchs, and Etta D. Pisano (MD). Technologies for Augmented-Reality Systems: realizing Ultrasound-Guided Needle Biopsies. Proceedings of SIGGRAPH 96 (New Orleans, La., Aug. 4-9, 1996), in Computer Graphics Proceedings, Annual Conference Series 1996, ACM SIGGRAPH, pgs. 439-446.

Another technique (disclosed in Edwards P J, Hawkes D J, Hill D L G, Jewell D, Spink R, Strong A, Gleeson M: Augmented reality in the stereo microscope for Otolaryngology and neurosurgical Guidance. Proceedings of MRCAS 95, Baltimore, USA, 1995, pp 8-15) uses an operating microscope as a device for overlaid display of 3D graphics. By "image injection" of stereoscopic structures into the optical channels of the microscope the surgeon sees the superimposed image over the surgical scene. This technique overlays simple meshes with a relatively low resolution onto the surgical scene, without providing any interactive capabilities. The authors report difficulties regarding the stereoscopic perception of the overlaid data in relation to the real view.

Although meant for guidance of the user, these techniques are all limited in application and usability.

SUMMARY OF THE INVENTION

The present invention aims to address at least one of the above problems, and to propose new and useful navigation systems and methods and devices for controlling them.

The present invention is particularly concerned with a system which can be used during a surgical operation. However, the applicability of the invention is not limited to surgical operations, and the systems and methods discussed below may find a use in the context of any delicate operation, and indeed during a planning stage as well as an intra-operative stage.

The present invention is motivated by noting that during the navigation procedure in a surgical operating room it is critical to be able easily and quickly to interact with a surgical navigation system, for example to alter the format of the computer-generated images. In addition, it would be advantageous to be able to simulate certain surgical procedures directly at the surgical site by using the computer-generated images.

In general terms, the present invention proposes a probe to be held by a user who performs an operation (e.g. a surgical operation) within a defined region while employing an image-based guide system having a display for displaying computer-generated images (3D and/or 2D slices) of the subject of the operation. The probe has a position which is tracked by the system and which is visible to the user (for example, because the system allows the user to see the probe directly, or alternatively because the computer-generated images include an icon representing its position). By moving the probe, the user is able to enter information into the system to control it, such as to cause changes in the physical shape of the subject in the image presented by the computer.

The invention proposes a guide system for use by a user who performs an operation in a defined three-dimensional region, the system including a data processing apparatus for generating images of the subject of the operation in co-registration with the subject, a display for displaying the images to the user, a probe having a position which is visible to the user, and a tracking unit for tracking the location of the probe by the system and transmitting that location to the data processing apparatus, the data processing apparatus being arranged, upon the user moving the probe to a selection region outside and surrounding the defined region, to generate one or more virtual buttons, each of the buttons being associated with a corresponding instruction to the system, the data processing apparatus being arranged to register a selection by the user of any of the virtual buttons, the selection including positioning of the probe in relation to the apparent position of that virtual button, and to modify the computer-generated image based on the selection.

The defined region is referred to as a "bounding box", so that the user is able to display the virtual regions by moving the probe out of the bounding box. This means that the amount of movement which a user has to perform to cause the virtual buttons to be displayed is low.

To indicate one of the virtual buttons, the user may move the probe to a location within that virtual button, but more preferably he may align a length direction of the probe in the direction of the desired virtual button (e.g. towards the centre of that button with a given tolerance). This latter possibility means that the probe only needs to be moved slightly to indicate one of the buttons. When this alignment has been made to indicate one of the buttons, the user may issue a separate confirmation command (preferably using a separate data input device which is not operated by the user's hand, such as a foot-operated switch) to confirm the selection. To help the user direct the probe accurately, a line may be displayed to the user extending from the probe along the length direction. The line may be a predefined length, or have a length controlled by the user (e.g. so that the user does not just indicate a virtual button by its direction but also by its distance from the probe).

Most preferably, the computer-generated images are overlaid on the real image of the subject and are preferably displayed in a semitransparent head-mounted stereo display (HMD), to be worn by a surgeon, so that he or she sees the computer-generated images overlying the real view of the subject of the operation obtained through the semi-transparent display (e.g. semi-transparent eye-pieces). The HDM is tracked, and the computer generates images based on this tracking, so that as the surgeon moves, the real and computer-generated images remain in register.

The system can be used in two modes. Firstly, during macroscopic surgery the user looks through the display in semi-transparent mode and sees stereoscopic computer graphics overlaid over the surgical field. This will enable the surgeon to see "beyond the normal line of sight" before an incision is made, e.g. visualising the position of a tumour, the skull base or other target structures.

Secondly, for microscopic surgery the same stereo display can be attached to (e.g. on top of the binocular of) a stereoscopic microscope, the position of which is tracked (as an alternative to tracking movements of the user). The computer graphics in the display may be linked to the magnification and focus parameters of the tracked microscope and therefore reflect a "virtual" view into the surgical field The 3D data presented in the display may be computer-generated by a computational neurosurgical planning package called VizDexter, which was previously published under the name VIVIAN and was developed by Volume Interactions of Singapore. VizDexter allows the employment of multimodal (CT and MRI fused) images in the Virtual Reality environment of the "Dextroscope" (for example, as disclosed in Kockro R A, Serra L, Yeo T T, Chumpon C, Sitoh Y Y, Chua G G, Ng Hern, Lee E, Lee Y H, Nowinski W L: Planning Simulation of Neurosurgery in a Virtual Reality Environment. Neurosurgery Journal 46[1], 118-137. 2000.9, and in Serra L, Kockro R A, Chua G G, Ng H, Lee E, Lee Y H, Chan C, Nowinski W: Multimodal Volume-based Tumor Neurosurgery Planning in the Virtual Workbench, Proceedings of the First International Conference on Medical Image Computing and Computer-Assisted Intervention (MICCAI), Massachusetts, Institute of Technology, Cambridge Mass., USA, Oct. 11-13, 1998, pp. 1007-1016. The disclosure of these publications is incorporated herein in its entirety by reference).

Although the invention has been expressed above in terms of a system, it may alternatively be expressed as a method carried out by the user of the system.

BRIEF DESCRIPTION OF THE FIGURES

The patent or application file contains at least one drawing executed in color (or grayscale). Copies of this patent or patent application publication with color (or grayscale) drawings will be provided by the Office upon request and payment of the necessary fee.

A non-limiting embodiment of the invention will now be described for the sake of example only with reference to the following figures, in which.

DETAILED DESCRIPTION OF THE EMBODIMENT

Prior to performance of a surgical operation using the embodiment of the invention, the patient is scanned, such as by standard CT and/or MRI scanners. The image series thus generated is transferred to the VR environment of the Dextroscope and the data is co-registered and displayed as a multimodal stereoscopic object, in the manner disclosed in the publications describing the Dextroscope referred to above. During the planning session in the Dextroscope, the user identifies relevant surgical structures and displays them as 3D objects (a process called segmentation). Additionally, landmarks and surgical paths can be marked. Before the actual operation the 3D data is transferred to the navigation system in the OR ("operating room", also known as "operating theatre").

Figure 1:
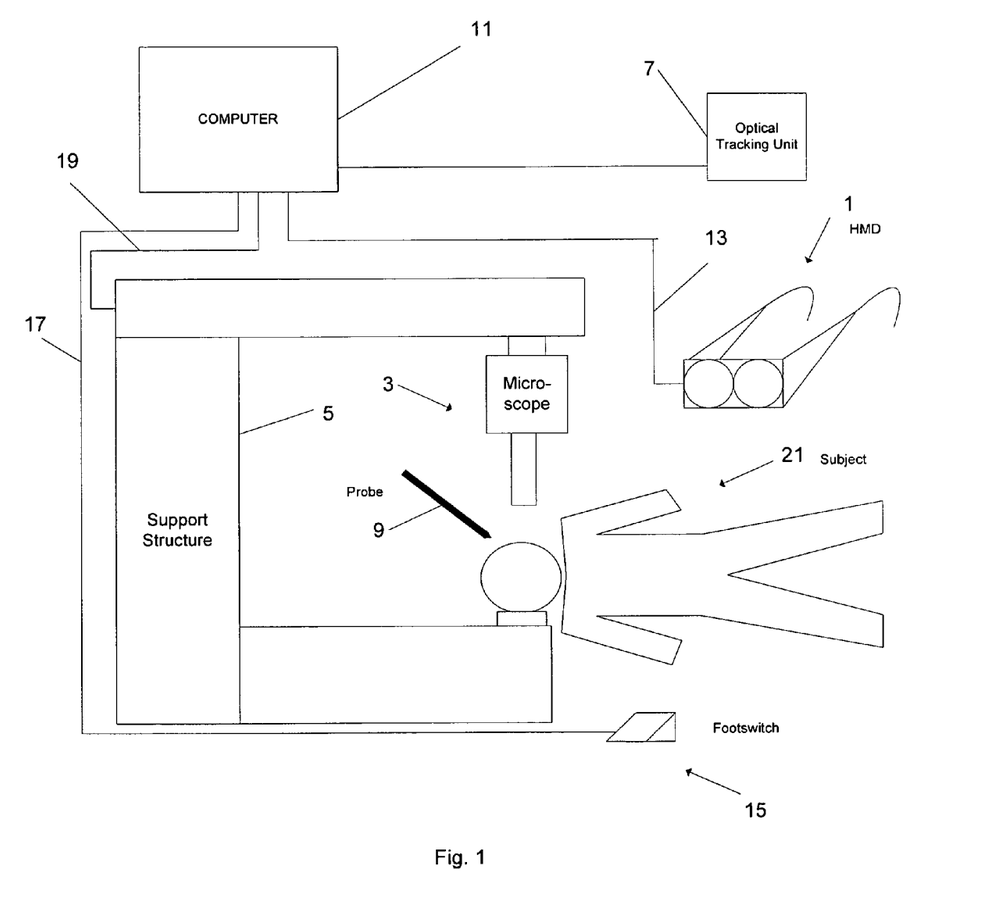
FIG. 1 shows a system which is an embodiment of the present invention in use during a surgical operation.

The system which is an embodiment of the present invention is shown schematically in FIG. 1, in which the various elements are not shown to scale. The system includes a stereo LCD head mounted display (HMD) 1 (we presently use a SONY LDI 100). The display may be worn by a user, or alternatively it may be mounted on and connected to an operating microscope 3 supported on a structure 5. The system further includes an optical tracking unit 7 which tracks the position of a probe 9, as well as the positions of the HMD 1 and the microscope 3. Such a tracking unit 7 is available commercially (Northern Digital, Polaris). The system further includes a computer 11 which is capable of real time stereoscopic graphics rendering, and transmitting the computer-generated images to the HMD 1 via cable 13. The system further includes a footswitch 15, which transmits signals to the computer 11 via cable 17. Furthermore, the settings of the microscope 3 are transmitted (as discussed below) to the computer 11 via cable 19. The subject of the operation is shown as 21.

We use a passive tracking unit 7, which operates by detecting three reflective spherical markers attached to an object. By knowing and calibrating the shape of an object carrying the markers (such as pen shaped probe 9), its exact position can be determined in the 3D space covered by the two cameras of the tracking system. In order to track the LCD display 1, three markers were attached along its upper frontal edge (close to the forehead of the person wearing the display). The microscope 3 is tracked by reflective makers, which are mounted to a custom-made support structure attached to the microscope 3 in such a way that a free line of sight to the cameras of the Navigation system is provided during most of the microscope movements. On top of the binocular, a second support structure allows the LCD display 1 to be mounted during microscopic surgery. The Polaris tracking unit 7 and the microscope 3 communicate with the computer 11 via its serial port. Connected to the another computer port is the footswitch 15 for interaction with the virtual interface during the surgical procedure.

The head of the patient 21 is registered to the volumetric preoperative data with the aid of skin markers (fiducials) which are glued to the skin before the imaging procedure and which remain on the skin until the surgery starts (normally a minimum of six fiducials are required). During the pre-operative planning procedure in the Dextroscope, the markers are identified and marked. In the operating theatre, a probe tracked by the tracking system is used to point to the fiducials in the real world (on the skin) that correspond to those marked on the images. The 3D data is then registered to the patient using a simple semi-automated registration procedure. The registration procedure yields a transformation matrix which transforms the virtual world to correspond to the real world. This registration procedure is standard in most modern neurosurgical navigation systems.

After completing the image to patient registration procedure, the surgeon wears the HMD 1 and looks at the patient 21 through the semi-transparent screen of the display 1 where the stereoscopic reconstruction of the segmented imaging data is displayed. The surgeon perceives the 3D data to be overlaid directly on the actual patient and, almost comparable to the ability of X-ray vision, the 3D structures appearing "inside" the head can be viewed from different angles while the viewer is changing position.

Firstly, we will explain the use of the system without the microscope 3. We refer to this as "STAR" (See Through Augmented Reality). We display the right and the left eye projection of the stereo image generated in the computer 11 on the right and the left LCD of the HMD 1 respectively. After calibrating the size of the patient's head and its distance to the HMD 1, the computer 11 generates an image that corresponds exactly to the surgeon's view of the real patient 21, which allows the surgeon to comprehend the exact correspondence between his surgical concepts developed during the planning and the actual patient 21. Having the virtual target structure in view, the surgeon is able to choose the ideal skin incision, craniotomy and path towards a lesion without ever having to look away from the surgery scene. The applications of STAR extend beyond neurosurgery, for example into the fields of cranio-facial or orthopaedic surgery, where the reconstructive bone work can be carried out more precisely under the virtual guidance of augmented 3D data generated during the planning session.

The user also sees a virtual probe which corresponds to the actual pen-shaped and tracked probe 9 in the surgeon's hand. With this probe the user activates and controls a virtual 3D interface, which allows interaction with the 3D data. The probe itself can also be turned into a unique simulation and navigation tool, as described below.

We now turn to navigation using the microscope 3, a phase referred to here as MAAR (Microscope assisted augmented reality). In this phase of the usage of the system of FIG. 1, the HMD 1 is attached to the support structure 5 above the microscope's binocular and the see-through mode of the HMD 1 is switched off, to just leave images supplied by the computer 11. These images are a combination of the stereoscopic video output of the microscope 3 (both right and left channel, transmitted to the computer 11 via cable 19) as well as the stereoscopic, segmented 3D imaging data generated by the computer 11 itself. The images are displayed in the HMD 1, and their respective signal intensity is adjustable by a video mixer. In order to navigate by means of the 3D data in the display the data needs to be exactly matched with the actual view through the microscope (or its video signal respectively). To do this, the computer 11 employs a knowledge of the settings of the optics of the microscope 3 to help generate the 3D graphics. The microscope's motor values for the zoom and focus are read from the microscope via the serial port (RS232 interface) and transmitted to the computer 11. Then the actual magnification and the plane of focus are calculated using predefined formulae. The position and the orientation (pose) of the microscope are obtained from the optical tracking system.

The computer 11 then generates a computer-generated image which matches the microscope magnification, plane of focus, and the viewpoint as a stereoscopic image of the 3D imaging data. This image is displayed in the HMD 1. Since the exact image is generated online, using the workings of the microscope optics, the surgeon can conveniently vary the zoom and focus values intra-operatively without the camera calibration or the system performance being affected. Since the microscope 3 is tracked in real time, the surgeon can freely move the microscope 3 around to get various viewpoints. By coupling the crop plane to the focus plane of the microscope 3, the user can slice through the virtual 3D imaging data planes by changing the focus values of the microscope.

In both STAR and MAAR, the interaction with the virtual objects is possible in real-time by using the tracked probe 9, which is displayed as a virtual probe within the computer-generated images presented to the user by the HMD 1.

Note that although the invention is explained above in terms of the images being fed into a HMD 1 which is separable from the microscope 3, an alternative within the scope of the invention is to overlaying the 3D computer-generated data directly onto the view through the microscope 3 by using an LCD based image "injection" system into the microscope's optical channels. In this case, there is no need for a separate HMD to perform MAAR During the navigation procedure, with either MAAR or STAR, the user sees the patient's 3D imaging data augmented over the real surgical scene. Especially since the virtual data usually consists of different imaging studies and their 3D segmentations (such as tumours, blood vessels, parts of the skull base, markers and landmarks) the user needs to be able to interact with the data during the operation in order to adapt it to the navigational needs. Tools are needed for example to hide/show or to control the transparency of 3D data, to adjust cropping planes, to measure distances or to import data. According to the present invention, the surgeon can interact with the computer 11 in this way to modify 3D data displayed in the HMD 1 by using only the passively tracked pen-shaped probe 9 and the footswitch 15, and thus circumventing the use of keyboard and mouse in the OR.

Figure 2:
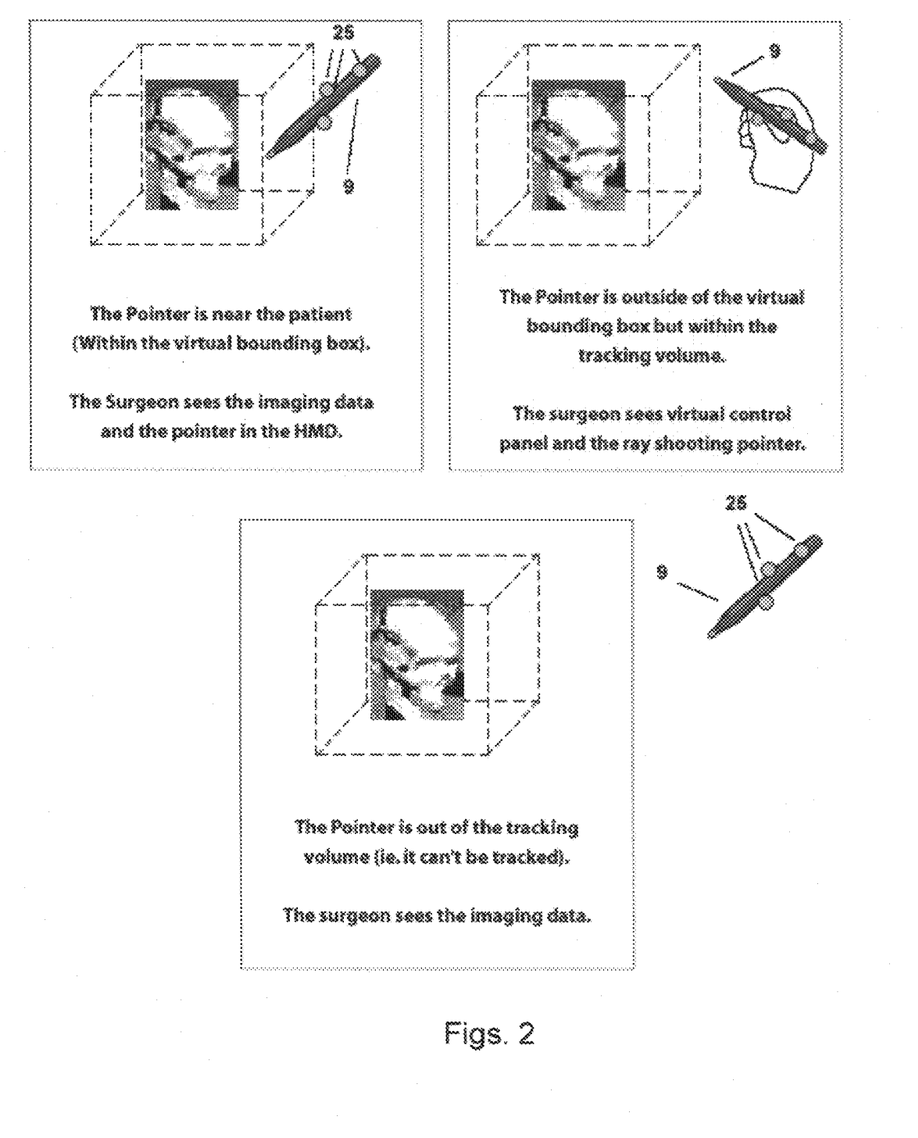
FIG. 2 shows the virtual bounding box and its relationship in the embodiment to the probe and the virtual control panel.

When the surgeon is moving the tracked probe near the patient's head, the probe 9 is within a virtual bounding box, which we have defined around the patient's head. This is illustrated in FIG. 2 (top left). The positions of the markers is shown as 25. The bounding box (which is in real space, not virtual space) is shown dashed, surrounding the region of interest in which the surgery occurs. In this situation, the computer-generated images show the user imaging data of the subject. Furthermore, a virtual probe corresponding to probe 9 is displayed in the HMD 1 in a realistically corresponding position to the virtual 3D imaging data.

When the probe is not visible to the tracking system, i.e. its reflective markers are hidden or it is out of the tracking volume, the virtual probe disappears and the surgeon sees only the augmented patient data displayed on the HMD. This is shown in FIG. 2 (bottom).

Figure 3:
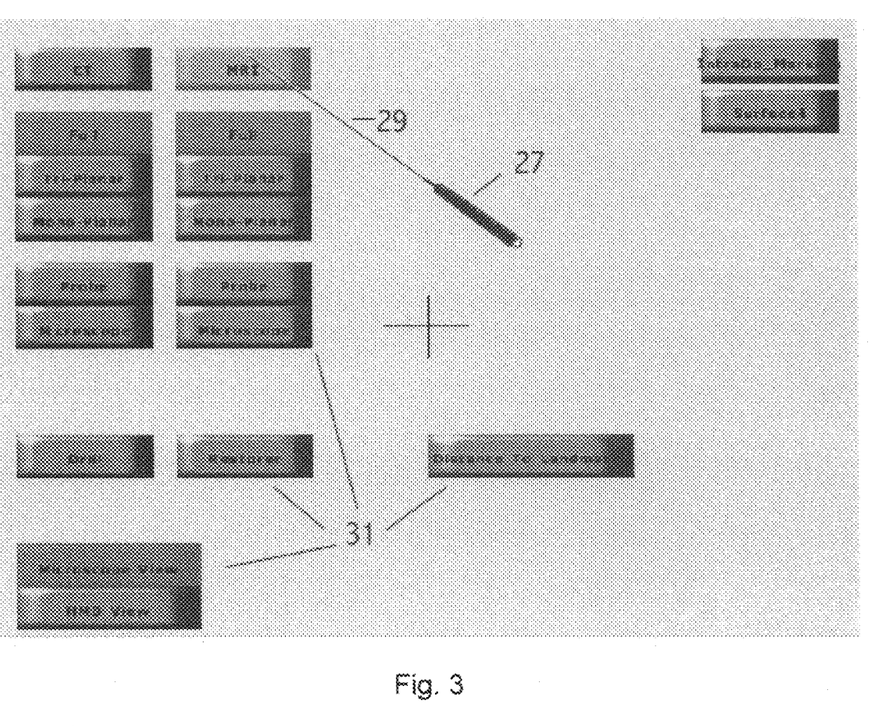
FIG. 3 shows the control panel as generated by the embodiment.

When the surgeon moves the probe 9 away from the patient's head and out of the virtual bounding box, but keeps it within the view of the tracking system (as shown in FIG. 2 (top right)), the visualization system switches the view so that the user only sees a computer-generated image which is a control panel. This panel is shown in FIG. 3. The virtual hand-held probe 27 is then displayed with a ray 29 shooting from its tip which makes it look like as a virtual laser probe in the virtual world. The buttons 31 on the control panel can be selected by pointing the virtual ray at them. Once selected, the buttons can be pressed (switched ON/OFF) using the foot-switch.

The control panel is placed such that when viewed in stereo it appears to be at a comfortable distance of about 1.5 m from the user. The virtual probe 27 itself reflects the movements of the real probe 9 in the surgeon's hand realistically, which results in the fact that the virtual buttons on the control panel can be pointed at with small wrist movements.

Figure 4:
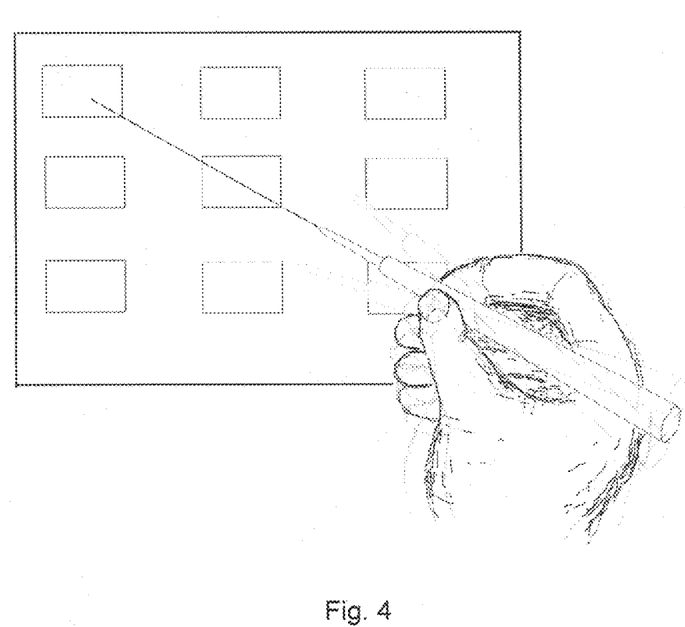
FIG. 4 illustrates a concept of small wrist movements controlling buttons on a distant panel in the embodiment.

In the space constraints of the operating room, especially while operating with the operating microscope, the described method of interaction enables the surgeon to comfortably and quickly access a wide range of navigation related tools. Important are two factors: Firstly, the fact that the virtual space, which activates the floating control panel, is surrounding the patient's head in close distance means that it can be reached by the surgeon with a simple arm movement in any direction away from the patient's head (as long as still being in view of the tracking system). The second important factor is that that once the virtual tool rack is visible, all its tools can be activated by small wrist movements instead of larger movements in the air which could conflict with the surrounding OR equipment. This is important since it allows the surgeon to navigate comfortable, even with his arms rested, while looking at the data in the display without the need to visually control his hand movements and thus without much distraction from the operative workflow. This effect is illustrated in FIG. 4, which shows a ray shooting from the probe's tip.

Within the virtual interface panel the surgeon has access to a suit of functionalities to modify the representation of the data, such as:

- Hide/Show the various imaging modalities and/or 3D objects. Operating in soft tissue for example makes it necessary to switch on some MRI derived segmentations (or the original MRI planes themselves) whereas the CT derived structures need to be switched on during bone work.
- Change the appearance of the data to mono-planar/tri-planar/3D full volume.
- Link the imaging data to the probe or the microscope. This means that the online-cropping plane (if the data appears as a 3D volume), the mono plane or the center point of a tri-planar image can be linked either to the focal plane of the microscope or to the virtually extendable probe (described below) which can be brought into the operative field.
- Activate the virtual probe and its virtual extension and retraction feature to control intra-operative simulation tools like a virtual drill and restorer tool, measurement tools or tools to simulate tissue retraction or clip placement (see 2.6).
- Activate a color and transparency adjustment table.
- Switch between the MAAR and the STAR systems.
- Activate tools to import and register intra-operative imaging data i.e. 3D ultrasound.

We have developed a method to turn the virtual probe into a tool, which allows some surgical steps to be navigated and simulated while interacting with the augmented data directly inside the surgical cavity.

Firstly, we will describe the novel navigation function of the embodiment. If volumetric 3D data is linked to the probe (by selecting it in the virtual tool rack, see above), a cropping plane perpendicular to the direction of the tip of the probe is generated. When the surgeon brings the probe to the surgical scene, and presses the foot-switch, the line extending from the probe is virtually elongated and the plane moves away from the tip of the probe (slicing through the patient data) to match the length of the line as long as the footswitch is kept pressed. Once the foot-switch is released the plane stays at the last position. When the foot-switch is pressed the next time, the line shortens and plane moves correspondingly towards the tip of the probe, until the foot-switch is released. This way the cut-plane can be moved in and out by alternately pressing the footswitch and various parts of the data can be examined. At each stage, the computer 11 generates data based on the cut-plane, e.g. as a mono-plane slice of the subject of the operation. The length of the virtual probe extension is displayed on-line to allow the measurement of distances in the depth of the operating cavity. If the data is chosen to appear as a monoplane, this isolated plane is also perpendicular to the probe and it can be moved in and out in the same fashion. If the data appears in tri-planar mode (i.e. as three orthogonal planes meeting at an origin), the triplanar origin is linked to the extendable probe.

Alternatively, and optionally, the data generated by the computer 11 can also be linked to the microscope settings and in this case the cutting plane is placed at the plane of focus of the microscope. This plane can then be moved by extending the line from the probe and/or using the focus button on the microscope.

Figure 5:
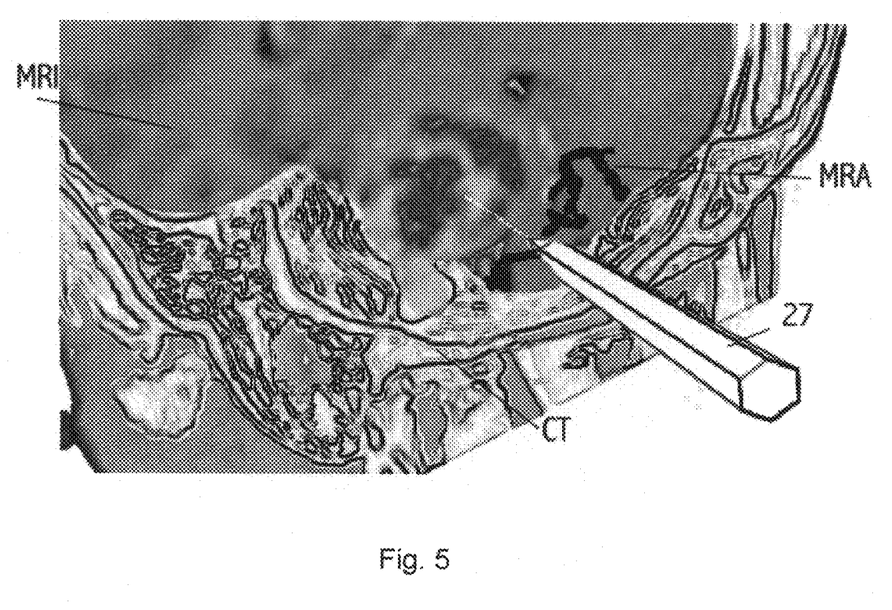
FIG. 5 shows use of the virtual extendible probe as a navigation tool in the embodiment.

FIG. 5 shows a computer generated image that combines three types of tissue. A bone which is volumetrically reconstructed from Computer Tomography (CT) data is shown in white and labelled CT. The Anglography (MRA) data, which shows the blood vessels, is displayed in the image in a second colour such as red (black in the picture). The Magnetic Resonance Imaging data (MRI) shows the soft tissue (in grey), and appears in mono-planar mode in a plane perpendicular to the virtual probe. The computer generated image of the MRI is cropped by being linked to the focal plane of the microscope. By extending the probe virtually the MRI plane moves into the depth of the operating field and the user can examine the spatial extent of a lesion (in this case a jugular schwannoma).

This tool can also be used to provide the surgeon with the online distance to surgically important landmarks placed during the planning stage (typically up to three or four). During navigation, a uniquely colored line is shown from the tip of the probe to each landmark, and the distance from each landmark is displayed next to each line. This display of landmarks can be turned ON/OFF using the floating control panel.

Figure 6A:
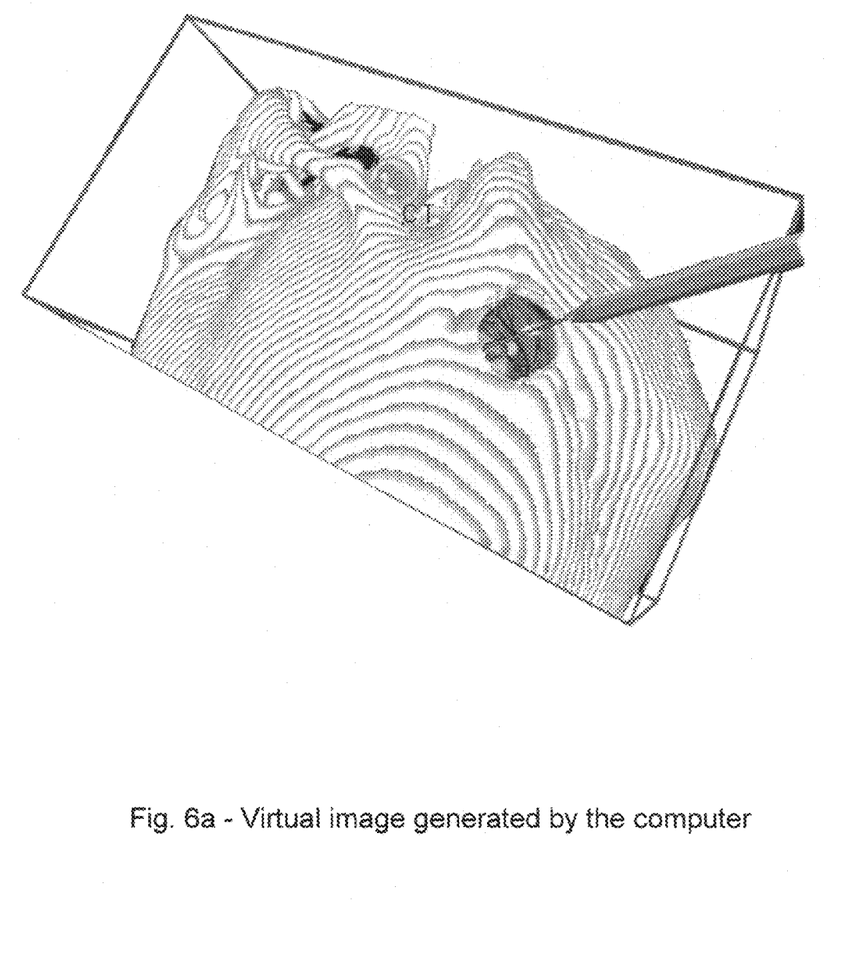
FIGS. 6a-c show use of the virtual extendable drill in a virtual operation using the embodiment.
Figure 6B:
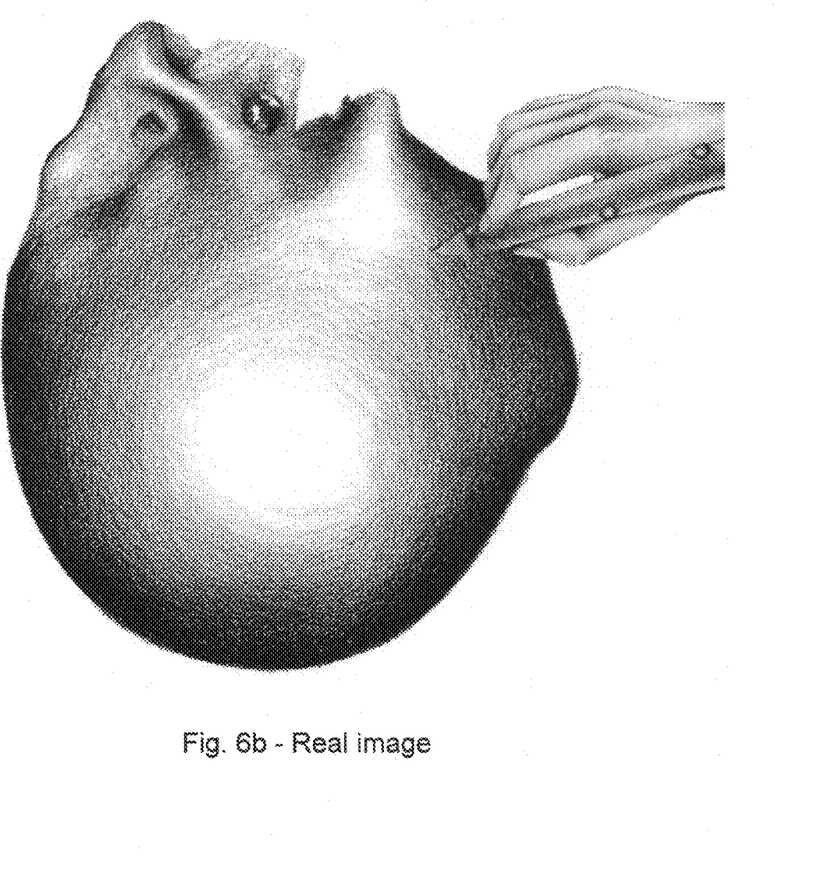
Figure 6C:
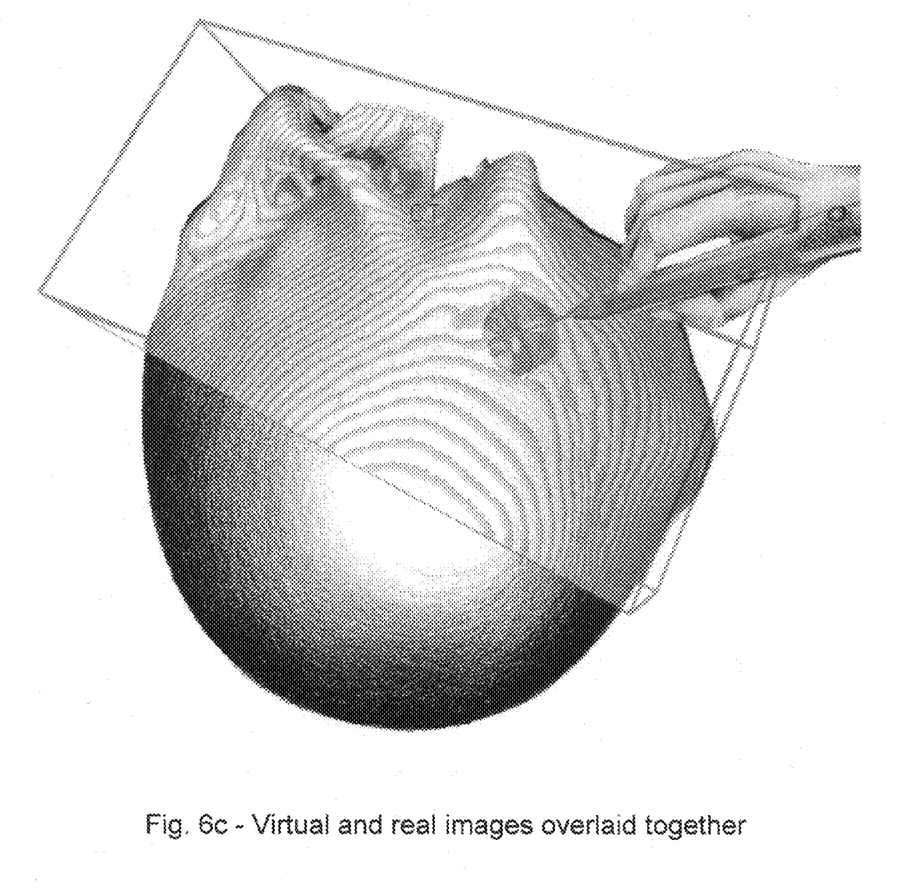

Secondly, we describe novel simulation function which can be performed using the present embodiment. The virtual drill tool consists of a virtual sphere which is attached to the virtual probe and which acts as a drill when introduced into the augmented virtual data by removing voxels (3D pixels) in real time. The spherical drill is virtually extendable and retractable by alternately pressing the foot-switch as described above, thereby changing the length of a line drawn extending between the probe and the spherical drill. The surgeon can thus drill at any point by moving the hand-held probe. The combination of real and computer-generated images seen by a user is shown in FIG. 6, in which FIG. 6a shows the virtual image of a skull of a patient together with the virtual tool, FIG. 6b shows the actual skull of the patient with the actual pen in the surgeon's hand which would in this case rest with its tip on the real bone or slightly above and FIG. 6c shows the view by the user through the user's head mounted display in which the virtual image of FIG. 6a is overlaid on and in co-registration with the real image of FIG. 6b and in which the visible cavity in the virtual bone has been drilled with the extendable voxel-removing sphere.

The system further includes a "restorer tool" which works is a similar fashion to the drill tool, except that it restores the voxels which were removed by the drill tool.

The intra-operative simulation tool provided by this embodiment is especially useful during the minute bone work at the skull base. It enables the surgeon to simulate bone removal along several directions by using the exactly overlaid 3D CT data. The optimal drilling path in relation to the surrounding structures can be explored and rehearsed virtually before the actual bone work is carried out. During the actual drilling, the overlaid virtually drilled data can be exactly followed. Apart from drilling, the described extendable virtual probe can also be used to simulate other surgical operations, such as to retract soft tissue or to place clips or bone screws virtually on the overlaid data before actually doing so during the surgery. It can be generally viewed as a tool, which allows the augmented 3D data to be probed and manipulated right at the surgical site in order to perform the actual subsequent surgical step more accurately and safely.

Although the invention has been explained above with reference to only a single embodiment, various modifications are possible within the scope of the invention as will be clear to a skilled person. For example, it is possible, though not preferable, to omit the representation of the line from the display of FIG. 6, showing only the tool and the probe; the line would still exist conceptually, however, as the controllable distance between the probe and the tool in the longitudinal direction of the tool.

The invention claimed is:

1. A guide system, comprising:
   a data processing apparatus for generating one or more images of a subject, said images being co-registered with the subject;
   a display for displaying the images to the user;
   a probe; and
   a tracking unit for tracking the location of the probe and transmitting said location to the data processing apparatus,
   wherein, said data processing apparatus generates said co-registered images of the subject in a main display area when the probe is within a defined three-dimensional visualization region, and upon a user moving the probe to a defined three-dimensional interface region outside of the visualization region, the data processing apparatus ceases to generate the co-registered images and causes the display in the main display area of an icon representing the probe and one or more virtual buttons, each of said virtual buttons being associated with a corresponding instruction to the system,
   and wherein the data processing apparatus is arranged to obtain a selection by the user of any of the virtual buttons, said selection effected by positioning the physical probe to position said icon relative to the apparent position of said virtual button, and to modify the generated images based on the selection.

2. A system according to claim 1 wherein the data processing apparatus is arranged to generate images of the subject of the operation overlaid on one of images of the subject and the subject itself.

3. A system according to claim 1 in which the positioning of the icon relative to the apparent position of said virtual button includes aligning a longitudinal axis of the probe in the direction of the button.

4. A system according to claim 3, wherein the data processing apparatus is arranged, while the virtual buttons are displayed, to include in the image a line extending from said icon.

5. The system of claim 4, wherein said icon is a virtual probe and is displayed as moving analogously to movements of the probe.

6. A system according to claim 2 in which the display is adapted to be mounted on the head of a user, the user being able to view the subject through the display, so as to see the one or more images generated by the data processing apparatus superimposed on a true image of the subject, the tracking unit monitoring the position of the display and transmitting the position of the display to the processing apparatus, which is arranged to modify the one or more images generated by the data processing apparatus according to the position of the display to maintain the one or more images generated by the data processing apparatus and the real image in stereoscopic registration.

7. A system according to claim 1 wherein the display is adapted to be mounted on a microscope, the user being able to view the microscope image through the display so as to see the one or more images generated by the data processing apparatus superimposed on the microscope image, the tracking unit monitoring the position of the microscope and transmitting the monitored position of the microscope to the processing apparatus, which is arranged to modify the one or more images generated by the data processing apparatus according to the position of the microscope to maintain the one or more images generated by the data processing apparatus and the real image in stereoscopic registration.

8. The system of claim 1, wherein the interface region is at least one of surrounding the visualization region, adjacent to the visualization region and distant from the visualization region.

9. The system of claim 8, wherein the interface region is within the tracking volume of the tracking unit.

10. The system of claim 1, wherein when the probe is within the visualization region the probe is co-registered to the subject and the icon is displayed in correct relative spatial position to the subject and said generated images of the subject.

11. The system of claim 1, wherein the image guided system is a surgical navigation system and the co-registered images are generated from scans of a human body.

12. A method of controlling an image guided system used in a defined three-dimensional visualization region, said system including a data processing apparatus for generating images of a subject in co-registration with the subject, a display for displaying the images to a user, a probe, and a tracking unit for tracking the location of the probe and transmitting that location to the data processing apparatus, said method comprising:

interacting with the image guided system in a display mode when the probe is within the visualization region, wherein images of the subject are displayed in a main display region; and interacting with the image guided system in a control mode when the probe is out of the visualization region but within a defined three-dimensional interface region;

wherein, when the probe is within the interface region the data processing apparatus obtains the position of the probe, ceases to generate the co-registered images, and generates in the main display area an image of an icon representing the probe and one or more virtual buttons, each of the virtual buttons being associated with a corresponding instruction to the system, wherein the user selects one of said buttons by positioning the physical probe in 3D space so as to position the representative icon relative to the apparent position of the button, and wherein the data processing apparatus sets or modifies display parameters for said display mode in response to the instruction corresponding to the selected button.

13. A method according to claim 12 wherein the data processing apparatus generates images of the subject overlaid on the subject.

14. A method according to claim 12 wherein while the data processing apparatus displays the icon and the virtual buttons, it further displays a line extending from said icon, and wherein the positioning of said icon includes aligning said line with the button.

15. A method according to claim 12 wherein the display is mounted on the head of a user, the user can view the subject through the display so as to see the generated images superimposed on a real image of the subject, the tracking unit monitors the position of the display and transmits said display position to the processing apparatus, which modifies the generated images according to the display position to maintain the generated images and the real image in stereoscopic registration.

16. A method according to claim 12 wherein the display is mounted on a microscope, the user can view the microscope image through the display so as to see the one or more images generated by the data processing apparatus superimposed on the microscope image, the tracking unit monitors the position of the microscope and transmits the microscope's position to the processing apparatus, which modifies the one or more images generated by the data processing apparatus according to the position of the microscope to maintain the one or more images generated by the data processing apparatus and the microscope image in stereoscopic registration.

17. The method of claim 12, wherein the image guided system is a surgical navigation system and the co-registered images are generated from scans of a human body.

\* \* \* \* \*